United States Patent
Ditrich et al.

US 7,829,702 B2
Nov. 9, 2010

(54) RACEMIC SEPARATION OF 2,6-TRANS-DIMETHYMORPHOLINE

(75) Inventors: Klaus Ditrich, Gönnheim (DE); Frank Haese, Dietzenbach (DE)

(73) Assignee: BASF SE, Ludwigshafen (DE)

( * ) Notice: Subject to any disclaimer, the term of this patent is extended or adjusted under 35 U.S.C. 154(b) by 308 days.

(21) Appl. No.: 12/159,504

(22) PCT Filed: Dec. 18, 2006

(86) PCT No.: PCT/EP2006/069862

§ 371 (c)(1), (2), (4) Date: Jun. 27, 2008

(87) PCT Pub. No.: WO2007/077118

PCT Pub. Date: Jul. 12, 2007

(65) Prior Publication Data

US 2009/0012289 A1  Jan. 8, 2009

(30) Foreign Application Priority Data

Dec. 30, 2005 (DE) .................. 10 2005 063 192

(51) Int. Cl.
*C07D 265/28* (2006.01)
(52) U.S. Cl. ..................... 544/106; 544/107
(58) Field of Classification Search ............. None
See application file for complete search history.

(56) References Cited

U.S. PATENT DOCUMENTS 4,571,424 A  2/1986  Christensen et al.

2004/0039206 A1  2/2004  Moher et al.

FOREIGN PATENT DOCUMENTS

DE  2822326 A1  11/1979
WO  WO-94/27966 A1  12/1994

OTHER PUBLICATIONS

Falbe, J., et al., "Mandelate", Römpp Chemie Lexikon, 1998, pp. 2516-2517.(See Translation).
"Milchsäure bis Petrolkoks", Ullmanns Encyklopädie der Technischen Chemie, 1980, vol. 17, pp. 451-457. (See Translation).
Müller, "A. Spaltung von Racematen", Methoden der Organischen, 1955, pp. 508-519. (See Translation).
Wilen, S. H., et al., "Strategies in Opitical Resolutions", Tetrahedron, 1977, vol. 33, pp. 2725-2736.
Licandro, E., et al., "Enantioselective Synthesis of (R)-(—)-Baclofen using Fischer-type Carbene Anions", Tetrahedron: Asymmetry, 2000, vol. 11, pp. 975-980.
Licandro, E., et al., "Improved Synthesis of (—)-(*2R,6R*)-2,6-Dimethylmorpholine", Gazzetta Chimica Italiana, 1997, vol. 127, pp. 815-817.

*Primary Examiner*—Kamal A Saeed
*Assistant Examiner*—Michael Barker
(74) *Attorney, Agent, or Firm*—Connolly Bove Lodge & Hutz LLP

(57) ABSTRACT

A process for preparing optically active trans-2,6-dimethylmorpholine by (i) reacting racemic trans-2,6-dimethylmorpholine with D-mandelic acid, (ii) removing the salt formed from D-mandelic acid and one enantiomer of trans-2,6-dimethylmorpholine from the other enantiomer of trans-2,6-dimethylmorpholine and (iii) isolating the desired optically active trans-2,6-dimethylmorpholine.

7 Claims, No Drawings

RACEMIC SEPARATION OF 2,6-TRANS-DIMETHYMORPHOLINE

RELATED APPLICATIONS

This application is a national stage application (under 35 U.S.C. §371) of PCT/EP2006/069862, filed Dec. 18, 2006, which claims benefit of German application 10 2005 063 192.4, filed Dec. 30, 2005.

The present invention relates to a process for preparing optically active trans-2,6-dimethylmorpholine by reacting racemic trans-2,6-dimethylmorpholine with optically active mandelic acid.

STATE OF THE ART trans-2,6-Dimethylmorpholine is an intermediate for the synthesis of fungicides and medicaments. Since, however generally only one enantiomer of trans-2,6-dimethylmorpholine has the sought-after biological activity, it is desirable to prepare trans-2,6-dimethylmorpholine in pure, optically active form.

This is done, for example, by a complicated enantioselective synthesis as described by Licandro et al. (Gazzetta Chimica Italiana 1997, 127, 815-817). There, (−)-(2R,6R)-2,6-dimethylmorpholine is prepared in a nine-stage synthesis from 1,2-propanediol.

This preparation is very cost-intensive and time-consuming; accordingly, there is a great need for alternative preparation methods which permit cheaper and more rapid access to optically active trans-2,6-dimethylmorpholine.

DESCRIPTION OF THE INVENTION

The present invention relates to a process for preparing optically active trans-2,6-dimethylmorpholine by (i) reacting racemic trans-2,6-dimethylmorpholine with optically active mandelic acid, (ii) removing the salt formed from optically active mandelic acid and one enantiomer of trans-2,6-dimethylmorpholine from the other enantiomer of trans-2,6-dimethylmorpholine and (iii) isolating the desired optically active trans-2,6-dimethylmorpholine.

Racemic trans-2,6-dimethylmorpholine can be isolated by fractional distillation from a mixture of trans- and cis-2,6-dimethylmorpholine, as obtainable by syntheses known to those skilled in the art.

The racemic trans-2,6-dimethylmorpholine is then reacted with optically active mandelic acid. For complete formation of the salt, 1 mol of optically active mandelic acid is added per mole of racemic trans-2,6-dimethylmorpholine. The mandelic acid can be added to the trans-2,6-dimethylmorpholine or vice versa. Preference is given to initially charging the mandelic acid and to adding racemic trans-2,6-dimethylmorpholine.

S,S-trans-2,6-Dimethylmorpholine crystallizes with D-mandelic acid; R,R-trans-2,6-dimethylmorpholine crystallizes with L-mandelic acid. The structure of the amine which has been crystallized out was determined by X-ray structural analysis.

A particular embodiment of the process according to the invention consists in adding up to 0.5 mol of optically active mandelic acid and up to 0.5 mol of another, achiral acid, preferably acetic acid, per mole of racemic trans-2,6-dimethylmorpholine.

This procedure has the advantage that one enantiomer of trans-2,6-dimethylmorpholine with the optically active mandelic acid forms the corresponding salt which precipitates out of the reaction medium, while the other enantiomer of trans-2,6-dimethylmorpholine, together with the optically inactive acid, for example acetic acid, remains in solution. This allows the enantiomers to be separated and isolated from one another easily.

The temperature of the process according to the invention is not particularly critical. It can be varied within a wide range. Preference is given to a temperature between 0° C. and the boiling point of the solvent employed, more preferably between 5 and 50° C. If desired, the reaction mixture can be cooled in order to remove heat of mixing which has arisen and/or to complete precipitations of salts.

The reaction can be carried out in many common organic solvents; preference is given to using alkanols as solvents. The process according to the invention proceeds with a particularly good yield using isopropanol as the solvent.

The salt formed in step (i) is removed preferably by crystallization and filtration of the crystals. To accelerate the crystallization, it is advisable to add some seed crystals. The crystals formed generally already have a high optical purity of above 70% de, preferably above 80% de (de=diastereomeric excess). In order to achieve a further increase in the optical purity, these salts can be recrystallized. For example, double recrystallization of the salts from isopropanol affords an optical purity of above 98% de.

The optically active R,R-trans-2,6-dimethylmorpholine can be released from the salt by adding a base, preferably sodium hydroxide solution, and isolated, for example, by distillation under reduced pressure.

The optically active S,S-trans-2,6-dimethylmorpholine can be isolated from the reaction solution as a salt and likewise released by means of base.

Under suitable conditions, it is possible also to recover the auxiliary reagent used for optical resolution—the mandelic acid—in optically active form.

The examples which follow serve to further illustrate and describe the invention.

Experimental Part

The general scheme of the process according to the invention is depicted below:

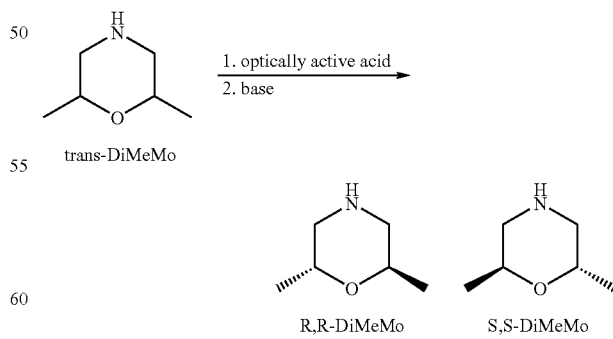

Optical Resolution on the Preparative Scale a. Precipitation of the R-Mandelate

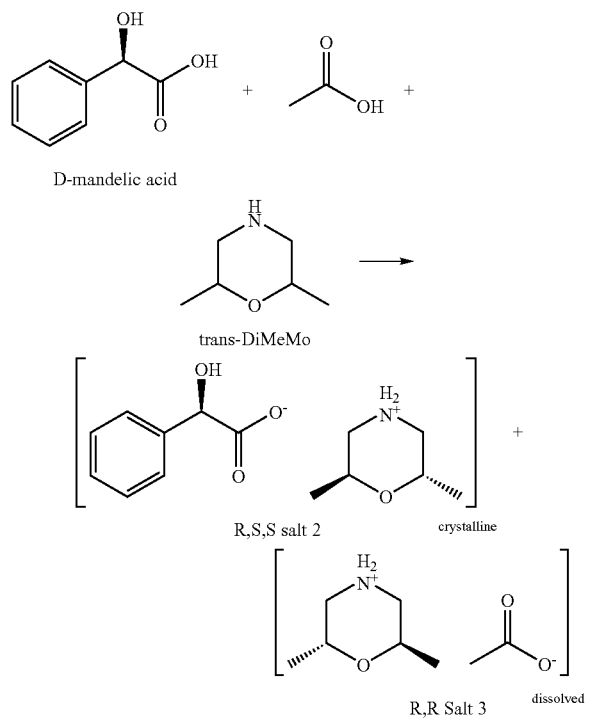

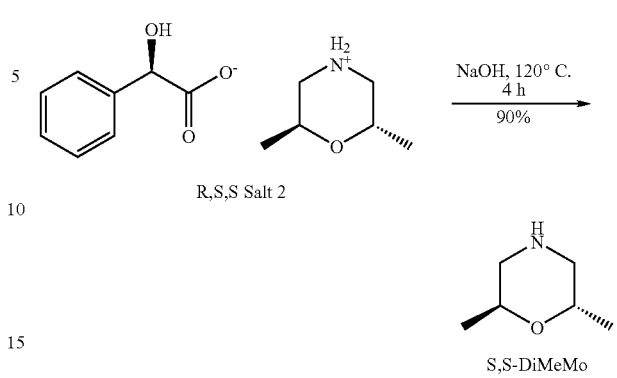

Procedure:

D-Mandelic acid (330.4 g, 2.174 mol) was initially charged in isopropanol (2 l), and admixed first with acetic acid (130.4 g, 2.174 mol) and then rapidly dropwise with trans-2,6-dimethylmorpholine (trans-DiMeMo, 500 g, 4.348 mol). In the course of this, the temperature of the mixture rose to 45° C. The clear solution was seeded with R,S,S salt 2 and left to stand at room temperature overnight. The next day, the mixture was cooled to 10° C. with stirring and the precipitated residue was filtered off with suction. The S,S-DiMeMo bound in the isolated R,S,S salt 2, (400 g (moist), 34%) had an optical purity of 74% ee. The salt was boiled in isopropanol (1 l), cooled to room temperature and seeded with one crystal of R,S,S salt 2. The mixture was left to stand at room temperature overnight and filtered with suction again the next day. 350 g (30%, moist) of R,S,S salt 2 were obtained; the S,S-DiMeMo bound therein had an optical purity of 97.7% ee. The salt was again dissolved in isopropanol (1 l) under warm conditions (70° C.) and left to stand at room temperature overnight. Again, the mixture was seeded with one crystal of R,S,S salt 2 and left to stand overnight. The precipitated salt was filtered off with suction and dried in a drying cabinet. 266.5 g (23%) of R,S,S salt 2 were obtained; the S,S-DiMeMo bound therein had an optical purity of 98.3% ee. The melting point of R,S,S salt 2 was 134° C.

The absolute configuration of the trans-2,6-dimethylmorpholine bound in the salt was determined by X-ray structural analysis (see appendix 1). According to this, S,S-DiMeMo is precipitated preferentially with D-mandelic acid.

b. Release of the S,S-2,6-dimethylmorpholine (S,S-DiMeMo) from the D-mandelate (R,S,S salt 2) Under Basic Conditions Procedure:

The D-mandelate (R,S,S salt 2, 266.5 g, 1 mol) was dissolved in 20% sodium hydroxide solution (400 ml) and stirred at 50° C. for one hour. This resulted in a clear solution. The bath temperature was increased to 120° C. and the released S,S-DiMeMo was distilled off in an azeotrope with water (at 100° C.) by means of a distillation apparatus. After approx. 300 ml of condensate had distilled over, the distillation receiver was cooled to room temperature and acidified with 10% HCl. The precipitated mandelic acid was filtered off with suction and dried under reduced pressure. An analysis of the optical purity showed that the D-mandelic acid had racemized fully.

The condensate which had distilled over was saturated by adding solid NaOH; an organic phase separated out and was diluted with MTBE (200 ml). Extraction was effected with MTBE (2×100 ml), and the extracts were combined, dried over $Na_2SO_4$ and concentrated by rotary evaporation. 101 g of crude product were obtained and were fractionated in a waterjet pump vacuum. The pure S,S-DiMeMo distilled over at 37-39° C./14 mm. 88 g (18% based on trans-DiMeMo racemate used) of S,S-DiMeMo were obtained as clear oil.

Rotation $[\alpha]_D = -6.15°$ (pure, $d=0.94$ g*cm$^{-3}$).

According to GC analysis, the optical purity of the isolated S,S-DiMeMo was 97.9% ee.

c. Precipitation of the S-Mandelate

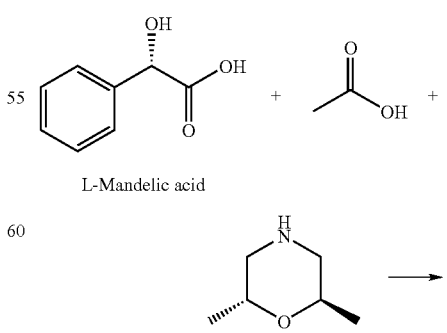

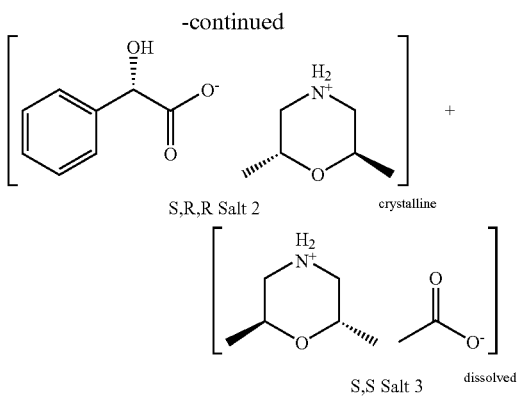

Procedure:

R,R-DiMeMo with an optical purity of 27.8% ee (S,S:R,R=36:64) was released from the mother liquors of the R,S,S salt 2 obtained in a. by the process outlined in b. In total, 312 g (74%) of this mixture were obtained.

L-Mandelic acid (312.5 g, 2.06 mol) and acetic acid (69.7 g, 1.16 mol) were initially charged in isopropanol (1500 ml) and admixed rapidly with trans-2,6-dimethylmorpholine (370 g, 3.21 mol, R,R:S,S=64:36). In the course of this, the temperature of the mixture rose to approx. 40° C. In the course of cooling to room temperature, the S,R,R salt 2 began to precipitate out. The mixture was left to stand at room temperature overnight and the precipitated salt was filtered off with suction the next day. 400 g (47% based on starting material used) of moist S,R,R salt 2 were obtained. The R,R-DiMeMo bound in the S,R,R salt 2 had an optical purity of 81.5% ee. The salt was dissolved in isopropanol (1 l) and left to stand at room temperature overnight. Again, the S,R,R salt 2 was filtered off with suction to obtain 320 g of S,R,R salt 2; the R,R-DiMeMo bound therein had an optical purity of 95.6% ee. The salt thus obtained was once again recrystallized from isopropanol (900 ml), filtered off with suction and dried under reduced pressure. 274 g were obtained (50% based on R,R-dimethylmorpholine R,R-DiMeMo used). The R,R-DiMeMo bound therein had an optical purity of 99.1% ee.

d. Release of the R,R-2,6-dimethylmorpholine (R,R-DiMeMo) from the L-Mandelate (S,R,R Salt 2) Under Acidic Conditions

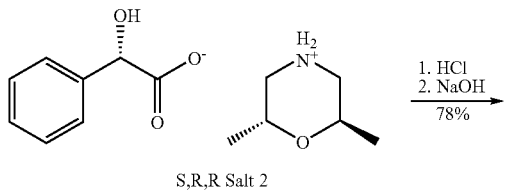

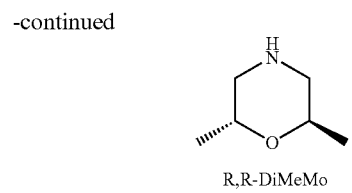

Procedure:

The L-mandelate (S,R,R salt 2, 274 g, 1.03 mol) was dissolved in water (400 ml) and brought to pH 1.5 by adding concentrated hydrochloric acid. The mixture was cooled to 1° C. and seeded by adding a few crystals of S-mandelic acid. The mixture was stirred at 0° C. for a further 2 hours and the precipitated crystal slurry was filtered with suction. The filter residue was washed with ice-water (100 ml) and dried at 50° C. under reduced pressure. 86 g (57%) of L-mandelic acid were obtained, which were optically pure according to analysis.

The combined filtrates were basified with ice cooling by adding solid NaOH (pH 14). When t-butyl methyl ether (300 ml) was added, a white greasy solid precipitated out. The organic phase was decanted off and the mixture was stirred another three times with t-butyl methyl ether (3 times 100 ml). The organic phases were decanted off in each case and the combined organic extracts were dried over sodium sulfate. The solvent was removed under reduced pressure and the residue was fractionated under reduced pressure. The pure R,R-DiMeMo distilled over at 36° C./13 mm. 93.2 g (18.5% based on trans-DiMeMo racemate used) of R,R-DiMeMo were obtained as clear oil.

Rotation $[\alpha]_D$=6.28°(pure, $d$=0.94 g*cm$^{-3}$).

According to GC analysis, the optical purity of the isolated R,R-DiMeMos was 99.1% ee.

What is claimed is:

1. A process for preparing optically active trans-2,6-dimethylmorpholine comprising
   (i) reacting racemic trans-2,6-dimethylmorpholine with optically active mandelic acid;
   (ii) removing the salt formed from mandelic acid and one enantiomer of trans-2,6-dimethylmorpholine from the other enantiomer of trans-2,6-dimethylmorpholine; and
   (iii) isolating the desired optically active trans-2,6-dimethylmorpholine.

2. The process of claim 1, wherein (ii) is achieved by precipitating the salt out of the reaction medium.

3. The process of claim 1, wherein (i) is carried out in isopropanol.

4. The process of claim 1, wherein up to 0.5 mol of optically active mandelic acid is used per mole of racemic trans-2,6-dimethylmorpholine.

5. The process of claim 4, wherein up to 0.5 mol of acetic acid is added in (i).

6. The process of claim 1, wherein S,S-trans-2,6-dimethylmorpholine is precipitated with D-mandelic acid.

7. The process of claim 1, wherein R,R-trans-2,6-dimethylmorpholine is precipitated with L-mandelic acid.

* * * * *